United States Patent [19]

Bastable et al.

[11] Patent Number: 4,807,987

[45] Date of Patent: Feb. 28, 1989

[54] DEEP CAVITY BINOCULAR LOUPE

[76] Inventors: David E. Bastable, 135 Walnut Ave., North Hampton, N.H. 03862; Trevor I. Goldberg, 3233 Landerwood Dr., Charlotte, N.C. 28210

[21] Appl. No.: 923,481

[22] Filed: Oct. 27, 1986

[51] Int. Cl.⁴ .............................................. A61B 3/10
[52] U.S. Cl. .................................................. 351/205
[58] Field of Search ................ 351/205, 214, 216, 221

[56] References Cited

U.S. PATENT DOCUMENTS

| | | | |
|---|---|---|---|
| 3,582,191 | 6/1971 | Cohen | 351/221 |
| 4,538,888 | 9/1985 | Sigelman | 351/205 |
| 4,682,866 | 7/1987 | Volk | 351/205 |
| 4,684,227 | 8/1987 | Schmidt et al. | 351/205 |

Primary Examiner—Rodney B. Bovernick
Assistant Examiner—Jay Ryan
Attorney, Agent, or Firm—John P. McGonagle

[57] ABSTRACT

A binocular instrument consisting of a binocular viewing system with convergence optics for reducing the parallax angle to one degree in combination with a fiber optics illumination system with adjustable lens and mirror system for projecting a spot of light to the surgical site, and detachable lenses for magnifying an observed image. The instrument is headband mounted. The magnification lenses are prefocused and easily attached or detached during a surgical procedure. The radial size of the projected light beam is adjustable by means of a manually controlled iris.

4 Claims, 3 Drawing Sheets

DEEP CAVITY BINOCULAR LOUPE

BACKGROUND OF THE INVENTION

This invention relates to optical instruments, and more particularly to an optical instrument of a binocular type arranged to be supported upon the head of a doctor, in proper position before the eyes of the doctor, and providing an illumination system for lighting objects to be viewed through the instrument.

Prior to this invention, Otolaryngologists had their choice of optical operating aids limited to general purpose types. These included large, floor-stand mounted microscopes with built in light sources; spectacle frame or headband mounted loupe-type magnifiers; fiber optic or incandescent light sources mounted on headbands; and ambient light reflectors. For most of these devices, changing features means changing headbands. The most useful of these devices for nasal surgery, specifically, would be the magnifying loupes coupled with a fiber optic light source mounted to a headband. These would be adequate for procedures done on a relatively flat field, but they do not give a stereoscopic view down deep, narrow cavities, such as nasal passages.

The binocular viewing body of the present invention has similarities to binocular indirect ophthalmoscopes such as found in U.S. Pat. No. 4,015,898 to K. E. Schirmer; U.S. Pat. No. 3,963,329 to J. G. Stumpf; U.S. Pat. No. 3,582,191 to D. N. Cohen, et al; and U.S. Pat. No. 2,757,574 to M. R. Thorburn. All contain a four mirror system which reduces the angle extending from the observed object and the left and right pupils of the observer. All contain eyepieces which can slide laterally to accomodate the interpupillary distance of the observer. The Stumpf ophthalmoscope comes closest to the present invention's viewing body. However, unlike Stumpf, with the present invention it is not necessary to set the eyepieces at a substantially greater distance than the ideal interpupillary distance to achieve an observation angle of less than one degree. This increases field of view and ease of use.

The magnification system of the present invention is designed so that lenses are readily attached to the front of the viewing body and to each eyepiece to form a Galilean telescopic system similar to the Poole attachment for the Keeler binocular indirect ophthalmoscope. The Poole attachment utilizes a variable focus system moving the viewing lens through a focusing range of 30–60 mm. This creates a superimposed zoom magnification range. However, to attain this magnification, the surgeon must move closer to the surgical site. This is a serious problem for an Otolaryngologist because of the resulting interference with his long, hand-held surgical instruments. The improvement in the present invention is that lenses of the present invention have various magnifications, but all are prefocused in the range of sixteen to twenty inches. This means that during a surgical procedure lenses of different magnifications may be interchanged without requiring a change in the working distance from the surgical site. This makes the present invention more suitable for ear, nose and throat surgery as opposed to the Poole/Keeler orientation toward eye surgery.

The present invention uses a fiber optics light source for illumination. There are several headband mounted devices for projecting and controlling the light from a fiber optics cable in the prior art. Included among the prior art are U.S. Pat. Nos. 4,290,422; 4,101,709; and 3,745,993. All such devices use one or more lenses to collect the light and project it as a spot to the surgical site. All use a mirror set at forty-five degrees between the cable and the exit lens to keep the unit compact and coaxial with the observer's line of sight.

The primary purpose of the present invention is to provide the Otolaryngologist a stereoscopic view down deep, narrow cavities while still providing a device useful for magnifying flat fields or for just illuminating a site. Present loupes, microscopes, and fiber optic light sources used for nasal surgery give a lighted view but with only one eye at a time since they do not reduce the interpupillary distance of the observer.

There are several types of indirect ophthalmoscopes that will reduce the interpupillary angle, and some that will also provide a magnified view of the surgical site like this invention. However, devices designed for eye surgery have serious drawbacks when used for nasal surgery. Eye surgery only requires use of the device for several minutes. Nasal surgery requires continuous use of the device for several hours. Ophthalmoscopes, especially those with magnifying attachments, are too large. They interfere with the long, hand-held surgical instruments used by Otolaryngologists. Ophthalmoscopes are also too hot and too heavy to be used continuously during hours-long procedures.

SUMMARY OF THE PRESENT INVENTION

The primary purpose of the present invention is to simplify and enhance surgical procedures where it is necessary to have light, magnification, and a reduced interpupillary angle, in various combinations, with minimal distraction to the surgeon. The present invention is designed primarily as an aid for ear-nose-throat surgery, but may also be used as a viewing aid for other procedures. Its features provide a well lit, stereoscopic, magnified view in deep cavities, such as the nasal cavity as far back as the Eustachion tube. It is headband mounted to allow freedom of movement. It is small so as not to interfere with hand-held surgical instruments, and so as to permit comfortable use for several hours. The instrument can be set up with a variety of magnification powers, or no magnification at all. The light source can be adjusted to allow direct lighted viewing without the convergent optics.

The invention is comprised of a binocular viewing body with eyepieces adjustable for individual interpupillary distance and a mirror system in front of the eyepieces for reducing the parallax angle from several degrees to one degree; detachable lenses for mangifying an observed image; an adjustable lens and mirror system for projecting a spot of light from a fiber optic cable to the surgical site; a comfortable, upholstered headband with adjustments for individual head sizes; and adjustable brackets connecting the light system and viewing body to the headband for positioning the invention in front of the user's eyes.

DESCRIPTION OF THE PREFERRED EMBODIMENT

Figure 1A:
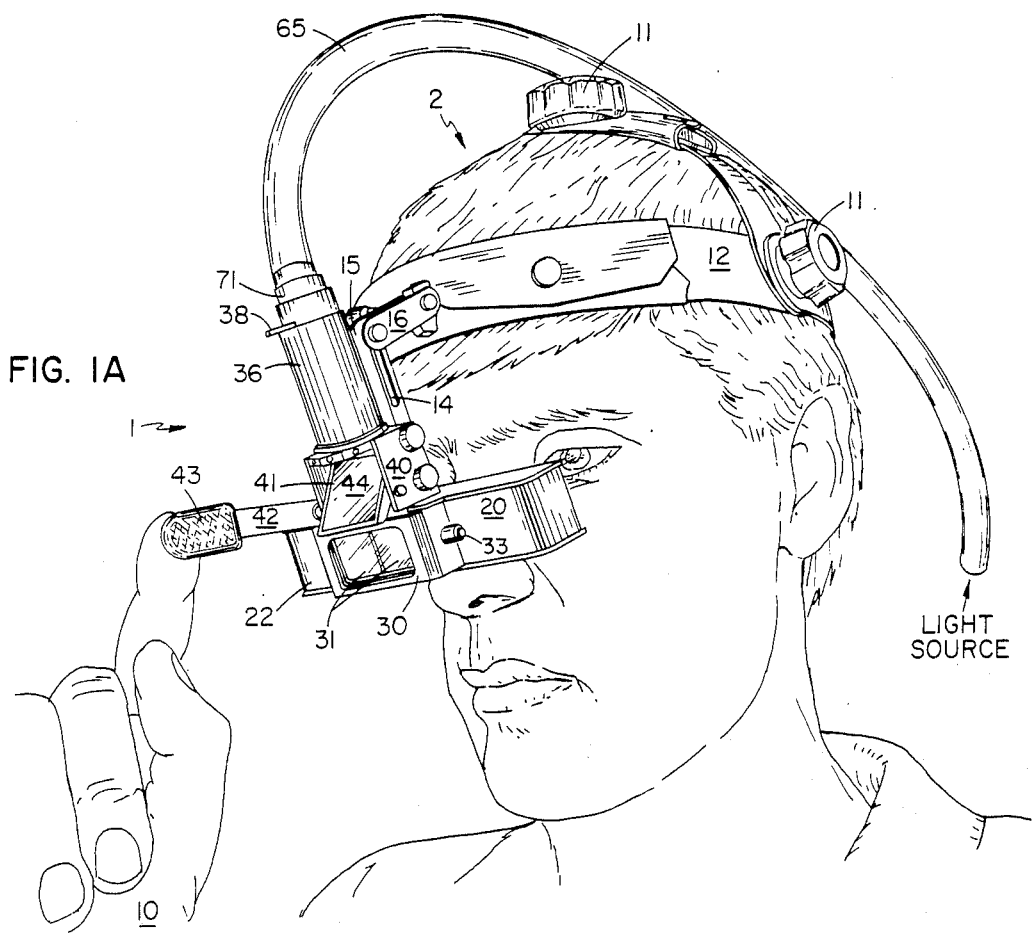
FIGS. 1A and 1B are front and side perspective views, respectively, of the present invention shown being worn by a user thereof.
Figure 1B:
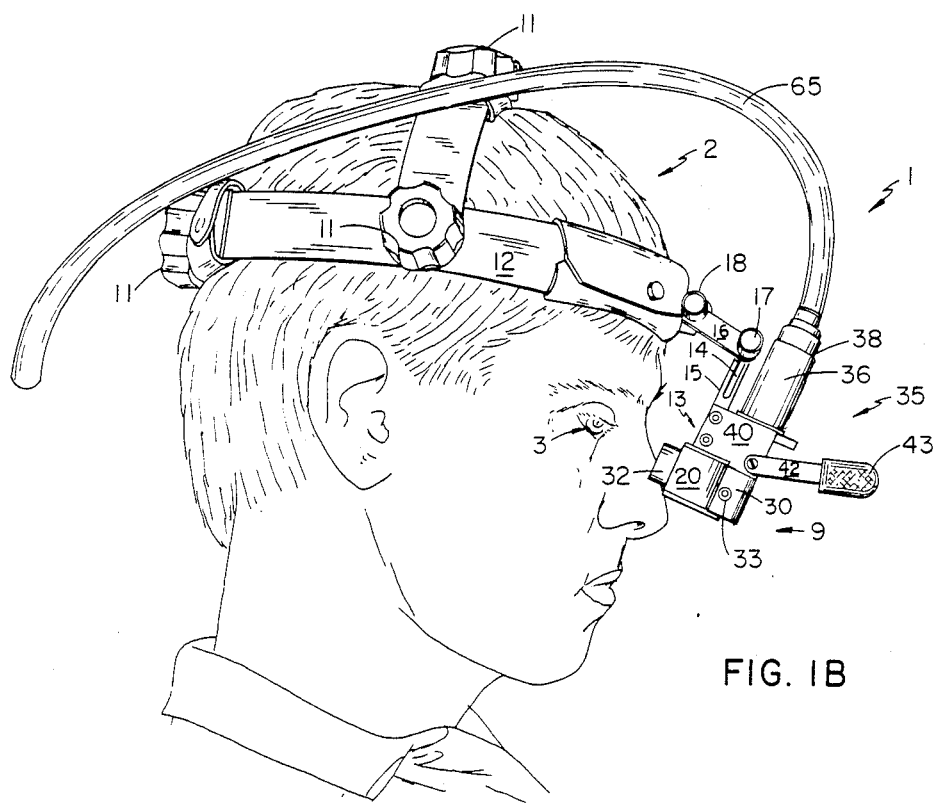

Referring more particularly to the drawings wherein like numerals indicate like elements, reference numeral 1 refers generally to the Deep Cavity Binocular Loupe comprising the present invention. Figures 1A and 1B are front and side perspective views, respectively, of the present invention 1 shown being worn by a user. Visible in these views are the user's head 2 with the invention 1 mounted thereon. The invention 1 is held on the user's head 2 by means of a comfortable, upholstered headband 12 with adjustments 11 for individual head sizes. Visible also in these views are the invention's viewing body 20, front magnification lens housing 30, light housing 36, and mirror housing 40. The illumination system 35 is comprised of the light housing 36 and the mirror housing 40 which contain adjustable lens and mirror system for projecting a spot of light from a fiber optic cable 65 to a surgical site X, Y or Z. The viewing body 20 contains a binocular mirror system for reducing the parallax angle from several degrees to one degree. The magnification system of the invention 1 consists of front magnification lenses 31 held in a housing 30, and rear magnification lenses 32 mounted on eye pieces 25 on the rear 26 of the viewing box 20.

The illumination system 35 is mounted on top of the viewing body 20 and both are attached to the headband 12 by means of two adjustable brackets, one approximately vertical 15 and one approximately horizontal 16. The front magnification lens housing 30 is attached to the front 22 of the viewing body 20 by means of spring loaded clips 33. Light 66 for the illumination system 35 comes to the light housing 36 from an external light source via a fiber optics cable 65. The mirror housing 40 has within it a mirror 41 externally manipulatable by the user's hand 10 via a small lever 42 attached to the side of the mirror housing 40. A sterile plastic sheath 43 may be slid over a portion of the lever 42 to help maintain operating room sterility. The adjustable brackets 15 and 16 roughly form an inverted "L". The illumination system 35 and viewing body 20 are both attached to the vertical bracket 15, with the vertical bracket 15 actually forming the back side of the mirror housing 40. The vertical bracket 15 is connected to the horizontal bracket 16 by means of a finger manipulated fastener 17. The horizontal bracket 16 is attached to the front of the headband 12 also by means of a finger manipulated fastener 18. This combination of headband adjustments 11 and adjustable brackets 15 and 16 will accomodate nearly every possible user desiring to use the invention 1.

Figure 2:
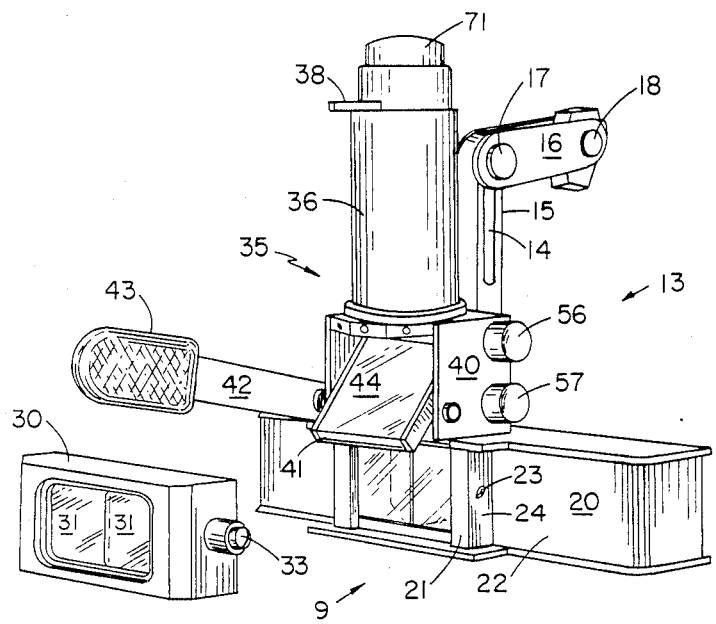
FIG. 2 is a front perspective view of the present invention without the headband and with the front magnifying lenses disconnected.
Figure 3:
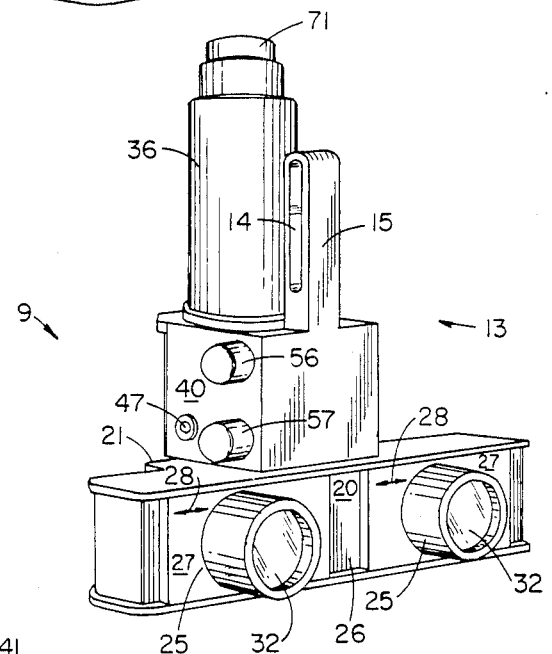
FIG. 3 is a rear perspective view of the present invention without the headband and one adjustable bracket.

FIGS. 2 and 3 are front and rear perspective views of the present invention 1 without the headband 12. FIG. 2 has the front magnification lens housing 30 disconnected from the viewing body 20. FIG. 3 is also missing the horizontal bracket 16. The viewing body 20 and illumination system 35 may be easily slid vertically upward by loosening the fastener 17. The slot 14 in bracket 15 will allow up to two inches of vertical adjustment. Referring to FIGS. 2 and 3, and also to FIGS. 1A and 1B, it can be seen that the overall horizontal angle of the invention 1 is adjustable primarily through changes in the horizontal bracket 15 by means of the fastener 18 at the headband 12. The front magnification lens housing 30 has a generally open rectangular shape with two magnifying lenses 31 mounted within in a plane generally parallel to the front 22 of the viewing body 20. The magnification housing 30 is mounted on the front 22 of the viewing body 20 by means of spring loaded clips 33. The viewing body 20 has a generally rectangular shaped protrusion 21 on its front 22 over which the magnification housing 30 fits. Indentations 23 on the protrusion sides 24 provide purchase for the magnification housing spring clips 33. The magnification system of the present invention 1 includes not only the front magnification lenses 31 held to the front of the viewing body 20 by the housing 30, but also rear magnification lenses 32 which slip over the two eyepieces 25 attached to the viewing body rear 26. The combination of the front magnifying lenses 31 and the rear magnifying lenses 32 form a Galilean telescopic system as can be most clearly understood from FIG. 6. The rear viewing eyepieces 25 are mounted on slides 27 for lateral adjustment 28 of the eyepieces to accomodate the interpupillary distances of various users. The front magnification lenses 31 are prefocused to a length in the range of fifteen to twenty inches.

Figure 4:
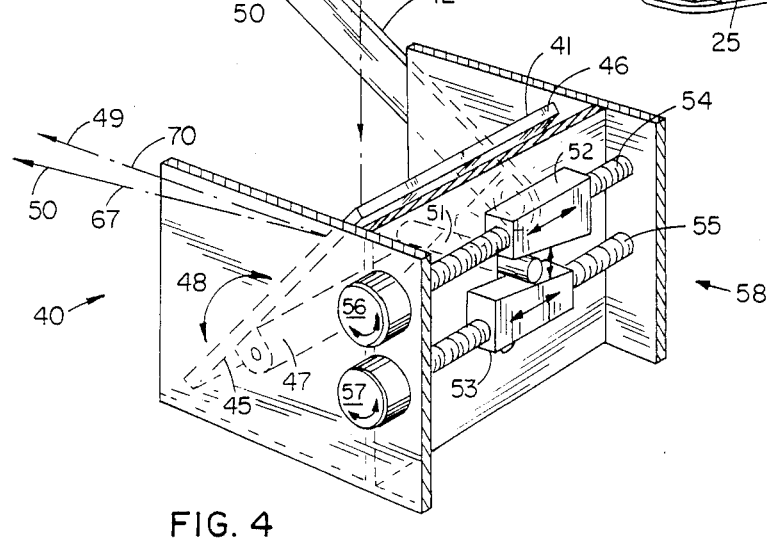
FIG. 4 is a fragmented rear plan view of the illumination mirror system from the general perspective of FIG. 3, but at a slightly different angle.
Figure 5:
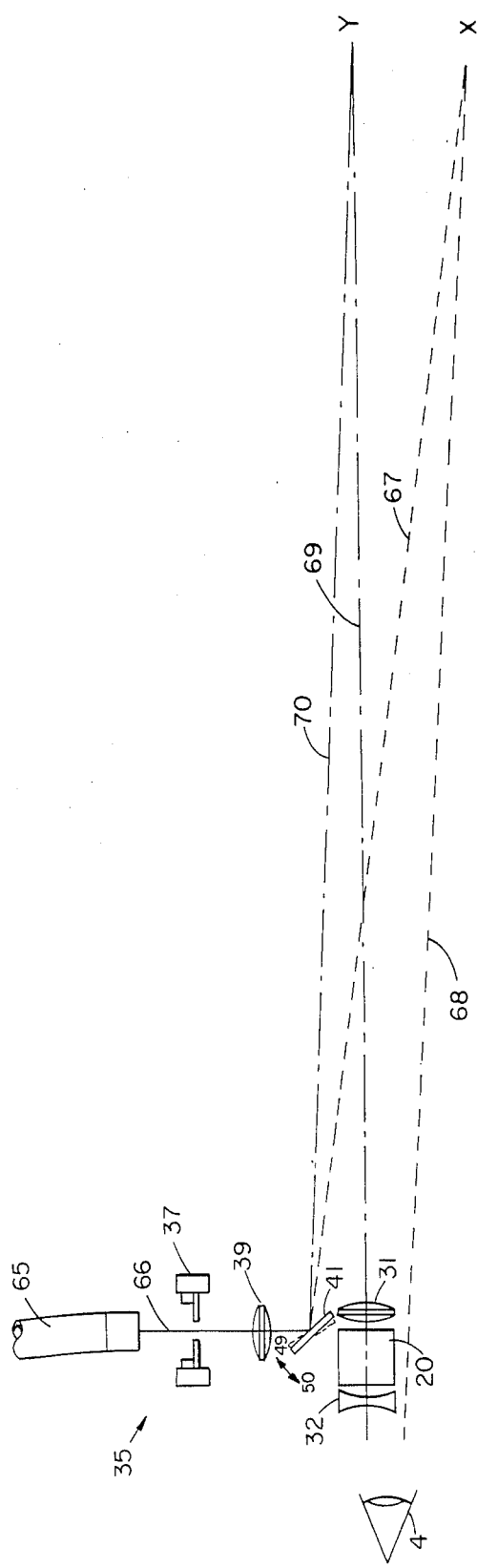
FIG. 5 is a side schematic view illustrating the relationship between the ocular and illumination optics of the present invention.
Figure 6:
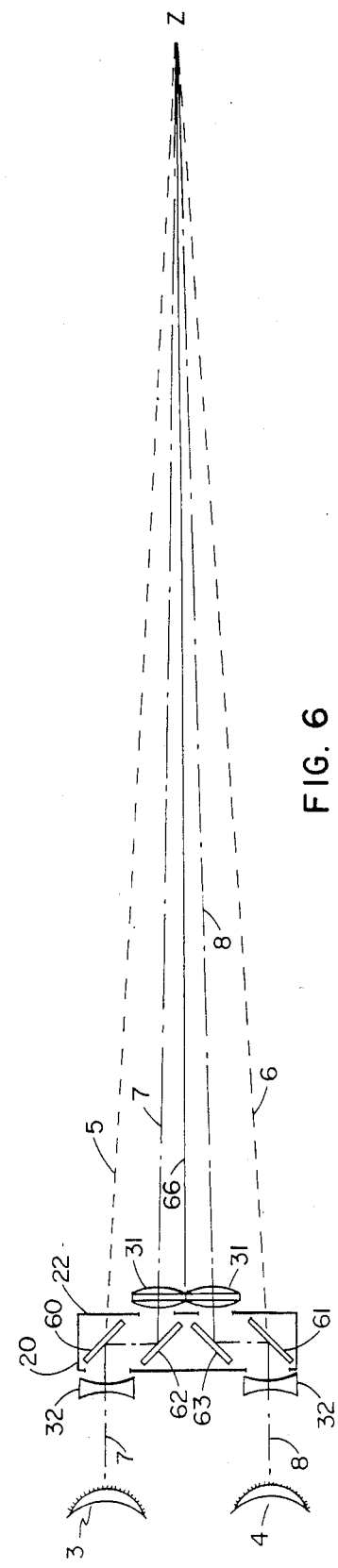
FIG. 6 is a top schematic view also illustrating the relationship between the ocular and illumination optics of the present invention.

FIG. 4 is a fragmented rear plan view of the mirror system contained within the mirror housing 40 from the general perspective of FIG. 3 but at a slightly different angle for increased clarity. FIGS. 5 and 6 are side and top schematic views, respectively, illustrating the relationship between the ocular and illumination optics of the present invention. Referring to FIGS. 4, 5, and 6 specifically, but also to FIGS. 1, 2, and 3 generally, light 66 for the illumination system 35 comes from an external light source via a fiber optics cable 65. The fiber optics cable 65 is friction joined to the invention 1 at the top 71 of the light housing 36. The light housing 36 contains an adjustable iris 37 and a collection and projecting lens 39. Light 66 from the fiber optics cable 65 beams through the iris 37 to the collection and projection lens 39 which focuses the light beam 66 on the mirror 41. The radial size of the light beam 66 is controlled by the iris 37. The iris 37 is externally adjustable by means of a small lever 38 visible near the top 71 of the light housing 36 in FIGS. 1A, 1B and 2.

The mirror housing 41 has two positions, one 49 for projecting the light beam while the user is using the viewing body 20, and the other 50 for projecting the light beam 66 when the viewing body 20 is not being used. When the viewing body 20 optics are being used the "optics" position 49 projects the light beam 66 at an approximate forty-five degree angle, and when the viewing body 20 is not being used the "nonoptics" position 50 projects the light beam 66 at an approximate forty-six degree angle. The lever 42 provides the user with position 49 or 50 control. The reflecting side 44 of the mirror 41 is used to position 49 or 50 the light beam 66. The mirror 41 is mounted on a bar 47 positioned along the axis of mirror movement 48. The bar 47 protrudes through the mirror housing 40 and is connected to the lever 42. Protruding from the mirror rear 45 is a rod 51. The rod 51 protrudes from the mirror rear 45 at a forty-five degree angle from the mirror top 46 while the mirror 41 is in the optics position 49. The rod 51 projects toward the rear 58 of the mirror housing 40 to a point between two wedge-shaped, adjusting blocks 52 and 53. The blocks 52 and 53 are mounted on adjusting rods 54 and 55, respectively, parallel to the mirror axis bar 47, but in a vertical plane near the mirror housing rear 58. The adjusting rods 54 and 55 have external control knobs 56 and 57, respectively, for moving the blocks 52 and 53 laterally along the longitudinal axes of the adjusting rods 54 and 55. The blocks 52 and 53 provide a stop position for the rod 51. The upper block 52 provides fine position control for the mirror's nonoptic position 50. The lower block 53 provides fine position control for the mirror's optic position 49.

The viewing body 20 contains a binocular four mirror system which reduces the angle extending from the observed object at the surgical site X, Y or Z to the left 3 and right 4 pupils of the user. The convergence optics of the viewing body 20 consist of left and right lateral mirrors 60 and 61 directly in front and at forty-five degree angles to the left 3 and right 4 eyes of the user. The lateral mirrors 60 and 61 converge the line of sight 7 and 8 of the left and right eyes 3 and 4 onto a prism type mirror arrangement 62 and 63 which reduces the parallax angle from several degrees, as defined by the paths 5 and 6, to one degree, as defined by the paths 7 and 8. The paths 5 and 6 are the normal viewing paths for the left and right eyes 3 and 4 without using the viewing box 20. The rear magnification lenses 32 are positioned between the user's eyes 3 and 4 and the lateral mirrors 60 and 61. The front magnification lenses 31 are positioned in front of the prism mirrors 62 and 63 between the convergence optics and the observed image Z. The convergence optics may be used with or without magnification as the front and rear magnification lenses 31 and 32 are easily removed or even changed without requiring the invention 1 to be removed from the head 2 of the user.

As may especially be noted in FIG. 5, the user may look directly at an illuminated point X in the surgical site Z without using the convergence optics in the viewing box 20. The lever 42 would be put in a down position corresponding to the nonoptics position 50 of the mirror 41. The light beam 66 would travel along the path 67 to point X. The user's line of sight would be along the path 68 to point X in the surgical site Z. Light 66 from the mirror would follow the path 67. By slightly adjusting the invention 1, the convergence optics of the viewing body 20 may be moved before the user's eyes 3 and 4. The lever 42 would be moved to the up position corresponding to the mirror's optics position 49. The light beam 66 would then travel along the path 70 to point Y. General line of sight would be along the path 69.

It is understood that the above described embodiment is merely illustrative of the application. Other embodiments may be readily devised by those skilled in the art which will embody the principles of the invention and fall within the spirit and scope thereof.

We claim:

1. A binocular instrument for use by otolarynogologists comprising:
    a binocular viewing body, having a front, back, and top, with eyepieces, laterally adjustable for individual interpupillary distances, mounted on the back of said viewing body, and with a mirror system within the viewing body in front of the eyepieces for reducing the pupillary parallax angle extending from an observed object in front of the viewing body to the left and right pupils of an observer from several degrees to one degree;
    detachable lenses for magnifying the observed object, the lenses being mounted on each eyepiece and on the front of the viewing body between the mirror system and the observed object;
    a lens and mirror system mounted on top of said viewing body for projecting a spot of light from a fiber optic cable to the observed object, said system containing an externally adjustable iris for varying the radial size of said spot of light, and an external switch for changing the mirror portion of said system to one of two present positions, one of which is for direct lighted viewing of the observed object with (optic) use of the binocular viewing body and the other of which is for direct lighted viewing of the observed object without (nonoptic) use of the binocular viewing body, and wherein the mirror portion of said lens and mirror system includes a flat mirror with two surfaces, the front surface of which is reflective and intercepts light from said fiber optics cable and reflects it to the observed object, and the back surface of which is attached to a radially rotatable horizontal bar attached to an external lever, said back surface also having a rod protruding therefrom to a point between two wedge-shaped blocks positioned in a vertical plane, whereby the optic lighted viewing position is established when said rod rests on the lower of said blocks and the nonoptic lighted viewing position is established when said rod rests against the upper of said blocks;
    a headband with adjustment means for individual head sizes; and
    adjustable brackets connecting the viewing body and lens and mirror system to the headband for positioning the instrument in front of the observer's eyes.

2. An instrument as recited in claim 1 wherein means for external fine adjustment of the mirror's horizontal angle in either switched position is provided by:
    said two wedge-shaped blocks each mounted on an individual adjusting rod, parallel to said mirror axis bar, but in a vertical plane to the rear of the mirror axis bar;
    external control knobs, one each attached to each adjusting rod, for moving said blocks lateral along the longitudinal axes of the adjusting rods; and
    whereby the upper block provide fine position control for the mirror's (nonoptic) lighted position and the lower block provides fine position control for the mirror's (optic) lighted viewing position.

3. An instrument as recited in claim 2, wherein:
    the detachable lenses mounted on the front of the viewing body are prefocused to a length in the range of fifteen to twenty inches.

4. An instrument as recited in claim 2, wherein:
    the said detachable lenses mounted on the front of the viewing body are attached to the front of the viewing body by means of spring loaded clips.

* * * * *